United States Patent [19]

Mishra

[11] Patent Number: 5,191,900
[45] Date of Patent: Mar. 9, 1993

[54] DIALYSIS PROBE
[75] Inventor: Pravin K. Mishra, Peoria, Ill.
[73] Assignee: The Board of Trustees of the University of Illinois, Ill.
[21] Appl. No.: 683,080
[22] Filed: Apr. 10, 1991
[51] Int. Cl.[5] ............................................. A61M 25/00
[52] U.S. Cl. ....................................... 128/769; 604/29; 604/43; 604/96; 128/768
[58] Field of Search ....................... 604/43, 27, 28, 96; 128/768, 769

[56] References Cited

U.S. PATENT DOCUMENTS

| | | | |
|---|---|---|---|
| 4,222,869 | 9/1980 | Kato | 604/28 X |
| 4,437,856 | 3/1984 | Valli | 604/43 X |
| 4,594,326 | 6/1986 | Wade | 128/768 X |
| 4,723,941 | 2/1988 | Thistle et al. | 604/27 X |
| 4,994,072 | 2/1991 | Bhate et al. | 604/96 X |

FOREIGN PATENT DOCUMENTS 2734248  2/1979  Fed. Rep. of Germany ........ 604/43

OTHER PUBLICATIONS

Abercrombie, E. D., et al., "Characterization of Hippocampal No repinephrine Release As Measured by Microdialysis Perfusion . . . ", *Neuroscience*, 27:897–904 (1988).
Benveniste, H., "Brain Microdialysis", *J. Neurochem.*, 52:1667–1679 (1989).
Benveniste, H., "Determination of Brain Interstitial Concentrations by Microdialysis", *J. Neurochem.*, 52:1741–1750 (1989).
Damsma, G., et al., "Automated Brain Dialysis of Acetylcholine in Freely Moving Rats: Detection of Basal Acetylcholine", *Life Sciences*, 41:873–876 (1987).
Hernandez, L., et al., "A Small, Removable Microdialysis Probe", *Life Sciences*, 39:2629–2637 (1986).
Korf, J., et al., "Amino Acids in Rat Striatal Dialysates . . . ", *J. Neurochem.*, 45:1341–1348 (1985).
Mishra, P. K., et al., "Selective Increase in Extracellular Nonrepinephrine and its Metabolites . . . ", *FASEB Abstracts*, 3:A293(390) (1988).
Mishra, P. K., et al., "Characteristics of Extracellular Norepinephrine . . . ", *Society for Neuroscience Abstracts*, 15:1227(482.17)(1989).
Philippu, A., "Use of Push-Pull Cannulae to Determine the Release of Endogenous . . . ", *Measurement of Neurotransmitter Release In Vivo*, pp. 3–37, (C. A. Marsden Ed.), John Wiley and Sons Ltd., (1984).
Robinson, T. E., et al., "Normalization of extracellular dopamine in striatum following recovery . . . ", *Brain Research*, 450:209–224 (1988).
Sandberg, M., et al., "Extracellular Overflow of Neuroactive Amino Acids During . . . ", *J. Neurochem.*, 47:178–184 (1986).
Ungerstedt, U., "Measurement of Neurotransmitter Release by Intracranial Dialysis", *Measurement of Neurotransmitter Release In Vivo*, pp. 81–105 (C. A. Marsden Ed.) John Wiley and Sons Ltd., (1984).
Westerink, B. H. C., et al., "Characterization of In Vivo Dopamine Release as Determined by Brain Microdialysis . . . ", *J. Neurochem.*, 51:683–687 (1988).
Westerink, B. H. C., et al., "Scope and Limitations of In Vivo Brain Dialysis: A Comparison of Its Application . . . ", *Life Sciences*, 41:1763–1776 (1987).
Yan, Q. S., et al., "Effects of Carbamazepine and Antiepilepserine on Dialyzable Norepinephrine and Serotonin . . . ", *Society of Neuroscience Abstracts*, 15:47 (24.8)(1989).

*Primary Examiner*—Peter A. Aschenbrenner
*Attorney, Agent, or Firm*—Marshall, O'Toole, Gerstein, Murray & Bicknell

[57] ABSTRACT

A microdialysis probe for living tissue having respective inlet and outlet, fluid impermeable tubes connected by a dialysis fiber membrane permeable only to small molecular weight compounds. A U-shaped, loop probe tip configuration of the fiber membrane contains a biologically inert wire insertion to prevent kinking and ensure continuous fluid flow through the tip. The length and/or inner diameter of the outlet tube is selected with respect to a given flow rate to create an optimum positive fluid pressure inside the probe membrane tip sufficient to self-support the membrane during insertion and dialysis sampling. Alternative side-by-side and concentric probe configurations are described.

14 Claims, 2 Drawing Sheets

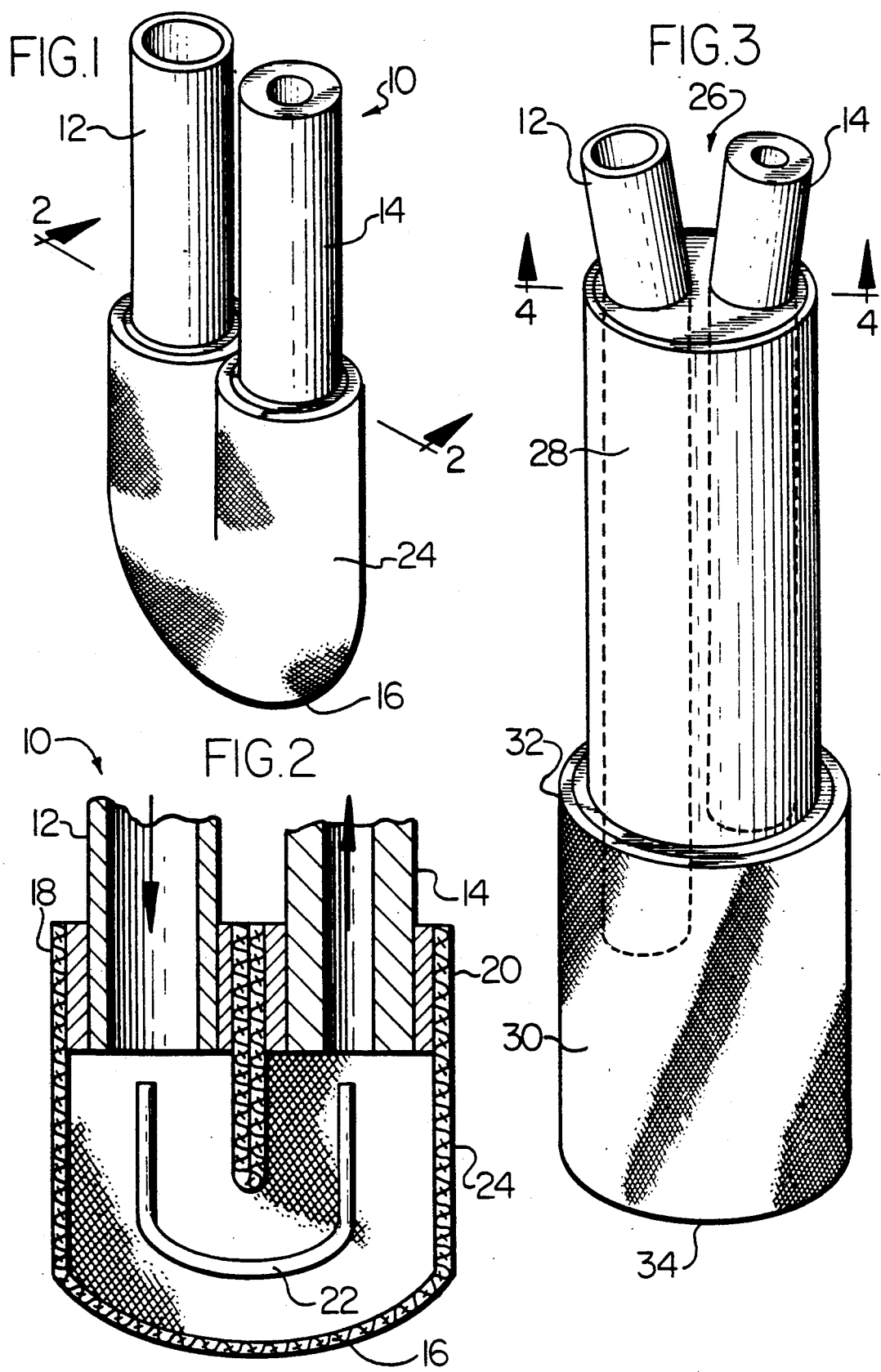

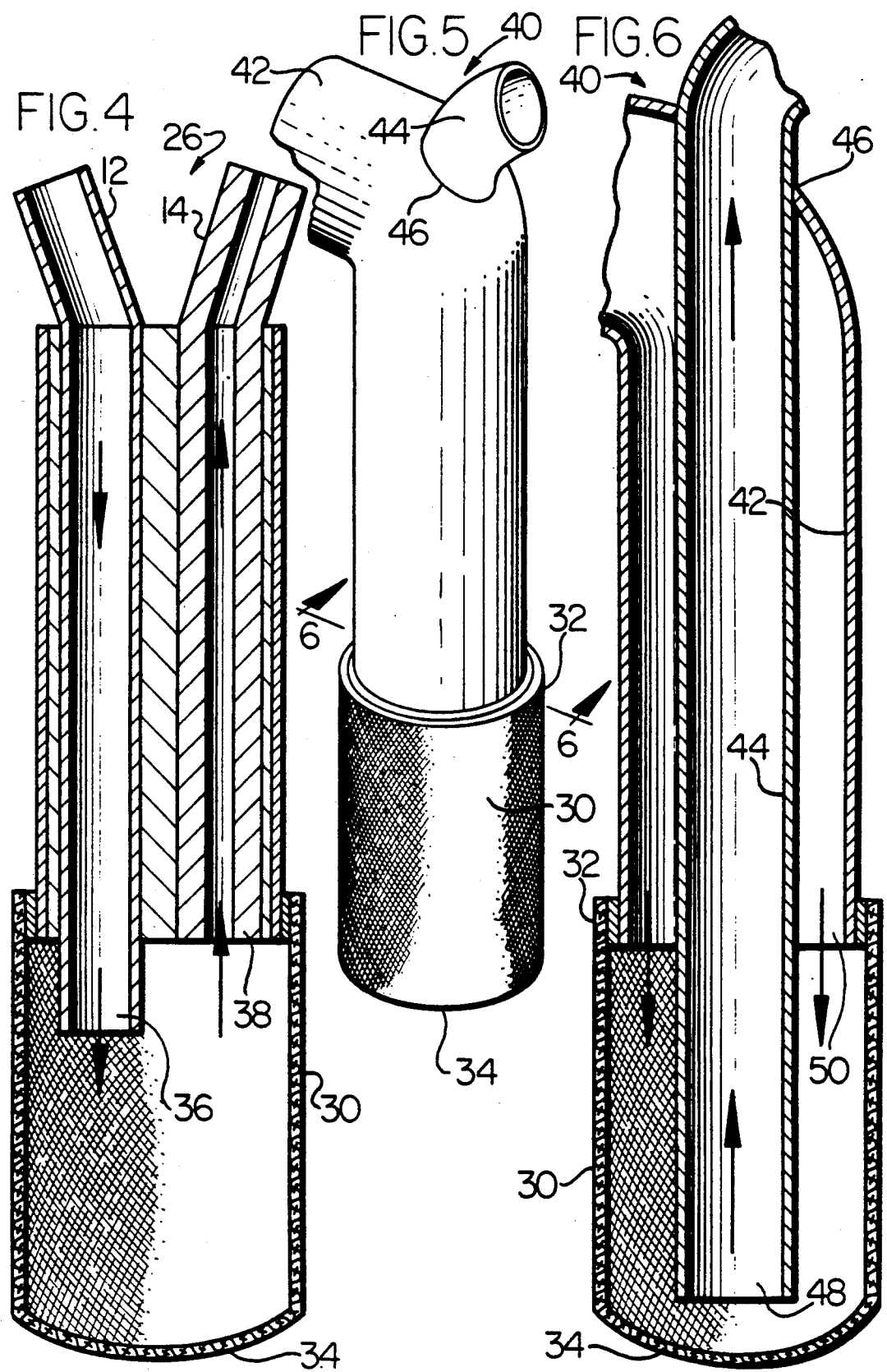

DIALYSIS PROBE

This invention relates to sampling probes for removing biological substances from living tissue, and in particular to small diameter probes useful for sampling small molecular weight compounds by performing microdialysis of the extracellular fluid of living tissue such as the brain, nervous tissue, and other such living tissue

BACKGROUND OF THE INVENTION

Biological fluid contained in the interstitial space of living tissue such as in the brain, nervous tissue, and other organs, often must be sampled for research and diagnostic purposes. Where ample fluid is available for sampling, generally direct withdrawal is practiced. However, in many instances, ample fluid is not available and the direct withdrawal technique cannot be used so that sampling must be achieved by indirect methods.

In one such indirect sampling technique, a medium fluid is injected in the region at the same rate as the "washed off" fluid is withdrawn. However, in the indirect sampling procedure, as well as in the direct sampling procedure, significant depletion of the chemical substances in the region of sampling occurs, or the prior sampling techniques often yield a sample of fluid which requires extensive treatment prior to analysis in order to attain worthwhile measurements.

Small diameter probes have been used to perform dialysis in living tissue as an alternative technique in an attempt to solve many of the aforementioned problems. This alternative technique is now known as "microdialysis". In microdialysis, the medium in which dialysis is performed can be made deficient of only the biological compounds which need to be sampled and the sampled biological compounds should be of a molecular structure small enough to pass through the dialysis membrane.

Prior devices which have been proposed or used for performing a dialysis sampling procedure have significant limitations with respect to reproducibility of test results and ease of insertion of the corresponding probes. Typically, such small diameter dialysis probes are introduced through appropriate insertion guides in the living tissue to be examined, and consist of essentially an inlet tube for supplying a continuous fluid flow, an outlet tube for removing fluid biological substances, and a dialysis membrane tip. The dialysis membrane is formed of a semipermeable material which is flaccid and extremely delicate when wet and easily collapsible. Accordingly, such probes are difficult to put in place, and potential inconsistencies in fluid flow because of possible deformations in the membrane produces inconsistent and unreliable test results. So called "loop" type dialysis probes, "side-by-side" and "concentric" probe configurations have been proposed in microdialysis probes, all of which have the aforementioned problems.

Prior attempts to solve these problems have not met with success. In some instances, the probe is inserted into the living tissue in a dry condition to avoid a flaccid fiber membrane. However, in such situations it is not known whether the probe will perform satisfactorily when fluid is pumped into the membrane during dialysis. Inoperability of such a probe requires the removal and reinsertion of an operable probe.

In other instances, an inflexible solid support of the dialysis membrane is provided using, for example, the fluid conducting tubes as the support member with only a window of an active dialysis membrane. In other instances, a skeleton-like support member is used to support the dialysis membrane during insertion of the probe and is then removed prior to the sampling dialysis procedure. These attempted solutions using either an external or internal support for the dialysis membrane contain one or more of the following limitations:

1. Limit the application of the probes in procedures with straight insertions into the living tissue since insertions through complex shaped insertion guides is impossible;
2. Cause a significant obstruction in flow path;
3. Require removal prior to use in order to allow a direct contact of the membrane with the biological fluids.

It is therefore desirable to provide a microdialysis probe which overcomes all of the disadvantages of prior known devices and which provides reliable and consistent test results.

SUMMARY OF THE INVENTION

In accordance with the principles of the present invention, a microdialysis probe is provided containing an inlet tube, an outlet tube, and a dialysis fiber membrane having membrane support means for subjecting the membrane to an effective optimum positive fluid pressure from the normal continuous fluid flow through the probe, sufficient to reliably self-support and maintain the shape of the membrane during insertion and dialysis sampling without requiring a physical support structure to maintain the membrane shape.

The membrane support means for subjecting the membrane to an effective optimum positive fluid pressure is provided partial restriction of the continuous fluid flow beyond the dialysis membrane. This is achieved by adjusting the physical characteristics of the outlet tubing with respect to the desired fluid flow rate. The inlet and outlet tubing utilized in the present invention are each of small diameters resulting in a significant reduction in the size of the insertable probe portion and enabling the use of a relatively small outlet tube for collection of samples to eliminate undesired "dead" volume from the system.

In a preferred form of the invention, extremely narrow bore and cylindrical inlet and outlet tubing are utilized so that the optimum positive pressure differential can be created by either reducing the diameter of the outlet tubing, by increasing the fluid flow rate, and/or reducing the length of the outlet tubing, either singularly or in various combinations.

The relationship between these several factors and the fluid pressure, P, inside an extremely narrow bore, cylindrical tubing is given by the following equation:

$$P = 8VLQ/\pi R^4;$$

where $8/\pi$ is the constant of proportionality; $V$ is the viscosity of the fluid; $L$ is the length of the tubing; $Q$ is the fluid flow rate; and $R$ is the radius of the tubing. Thus, it can be seen that a variety of combinations of the aforementioned parameters can be used to create the optimum positive pressure sufficient to reliably support and maintain the shape of the dialysis membrane during insertion and sampling without requiring a physical support structure to maintain the membrane shape in accordance with the present invention.

Using the principles of this invention, a loop type probe, a side-by-side probe, or a concentric probe configuration can be provided. In a constructed preferred loop type embodiment, a suitable length of fused silica tubing of 75 micron inner diameter was used as the inlet tubing. The outlet tubing consisted of an initial 10 cm length of fused silica tubing of 50 microns inner diameter connected to a 100 cm length of fused silica tubing of 75 microns inner diameter. A 1.6 cm cylindrical section formed of a cellulose acetate dialysis fiber of 6,000 Daltons permeability limit was connected to the inlet and outlet tubing and bent at the middle to form a U-shaped loop tip at the probe bottom.

A Teflon coated thin metal wire inserted within the loop does not provide any skeletal support but acts to prevent kinking of the loop formed in the membrane and thereby tends to keep the desired unrestricted fluid flow across the tip of the loop. The preferred embodiment was used with a flow rate of 1.0 $\mu$l/min. The dead volume of the fiber membrane portion of the device should be appropriately adjusted to the fluid flow rate in order to permit a continuous replacement of the profusion medium. The extent of diffusion and/or dialysis across the membrane is related to the velocity of the dialysis medium through the fiber membrane. Thus the flow rate of the fluid medium has upper and lower limits.

In an application of sampling of brain monoamines for example, the higher the flow rate, the lower is the concentration of monoamines inside the fiber membrane as well as in the collection vessel. However, due to a low concentration inside the fiber at the time of dialysis, more amounts of monoamines in absolute quantities will pass through the membrane, yielding more absolute amounts in the collection vessel. In other words, an extremely small flow rate would result in a higher concentration of monoamines in the recovered fluid due to availability of time while the profusion fluid is passing through the membrane. However, due to an increased concentration inside the profusion fluid, the total amount of monoamines diffusing into the probe will be less. Thus, the sensitivity of the analytical instrumentation and concentration of the desired substance determine the optimum flow rate.

Systems are under development for monoamine analysis which may have detection limits of <25 femto Mole. However, most common commercially available high-performance liquid chromatography systems equipped with electrochemical detection allow a precise analysis >200 fM amounts. A 3 mm probe, constructed accordingly achieves approximately 20–30% relative recovery of monoamine in vitro. Thus, in order to collect analyzable quantities of monoamines from most areas of the rat brain, a 15–45 minute sampling interval is required.

The absolute recovery of dialyzable substances is proportionate to and dependent on the surface area of the membrane and the time interval of sampling. Therefore, a change in flow rate does not have a significant impact on the absolute amount recovered in the operative ranges of flow rates. However, the upper and lower limits of flow rate are governed by the analytical requirements and handling precision of the fluid respectively. Reduction in the flow rate may have to be accompanied by an increase in collection interval as submicroliter volumes are difficult to handle. Also, an increase in flow rate beyond 10 $\mu$l/min would recover approximately identical absolute quantities of monoamines in a given duration but would be too dilute to be analyzed with most analytical techniques.

In accordance with the principles of the present invention, when using a cellulose acetate dialysis fiber membrane, a pressure differential of at least 80 mm Hg inside the dialysis membrane is required to support the membrane during insertion and sampling in accordance with this invention. The upper limit of fluid pressure should be that which is less than the amount which would cause the fiber membrane to undesirably inflate and perhaps burst. In the case of a cellulose acetate dialysis fiber, the upper limit fluid pressure should be maintained less than about 610 mm Hg. Therefore, when using a cellulose acetate dialysis fiber membrane, it is preferred that the fluid pressure be maintained at an optimum positive pressure of least about 80 and less than about 610 mm Hg.

As noted above, various combinations of tubing diameters and lengths of the outlet tubing can be used in order to generate the optimum fluid pressure inside the dialysis fiber membrane in accordance with the present invention. As an aid in utilizing the present invention to achieve the aforementioned optimum positive fluid pressure, the following Table illustrates the pressures generated inside the dialysis fiber membrane as a function of the fluid flow rate in $\mu$l/min and various lengths (cm) and internal diameters (microns) of the outlet tubing.

| | | Outlet Tubing | | | | | |
|---|---|---|---|---|---|---|---|
| Diameter ($\mu$) | Length (cm) | Flow Rate ($\mu$l/min) | | | | | |
| | | 0.5 | 1 | 2 | 3 | 4 | 5 |
| 25 | 1 | 65 | 131 | 261 | 392 | 523 | 653 |
| 25 | 10 | 653 | 1306 | 2613 | 3919 | 5226 | 6532 |
| 25 | 100 | 6532 | 13064 | 26129 | 39193 | 52258 | 65322 |
| 40 | 1 | 10 | 20 | 40 | 60 | 80 | 100 |
| 40 | 10 | 100 | 199 | 399 | 598 | 797 | 997 |
| 40 | 100 | 997 | 1993 | 3987 | 5980 | 7974 | 9967 |
| 50 | 1 | 4 | 8 | 16 | 24 | 33 | 41 |
| 50 | 10 | 41 | 82 | 163 | 245 | 327 | 408 |
| 50 | 100 | 408 | 817 | 1633 | 2450 | 3266 | 4083 |
| 75 | 1 | 1 | 2 | 3 | 5 | 6 | 8 |
| 75 | 10 | 8 | 16 | 32 | 48 | 65 | 81 |
| 75 | 100 | 81 | 161 | 323 | 484 | 645 | 806 |
| 100 | 1 | 0 | 1 | 1 | 2 | 2 | 3 |
| 100 | 10 | 3 | 5 | 10 | 15 | 20 | 26 |
| 100 | 100 | 26 | 51 | 102 | 153 | 204 | 255 |
| 200 | 1 | | | | | | |
| 200 | 10 | | | 1 | 1 | 1 | 2 |
| 200 | 100 | 2 | 3 | 6 | 10 | 13 | 16 |

| | | Outlet Tubing | | | | |
|---|---|---|---|---|---|---|
| Diameter ($\mu$) | Length (cm) | Flow Rate ($\mu$l/min) | | | | |
| | | 10 | 25 | 50 | 100 | 250 |
| 25 | 1 | 1306 | 3266 | 6532 | 13064 | 32661 |
| 25 | 10 | 13064 | 32661 | 65322 | 130645 | 326612 |
| 25 | 100 | 130645 | 326612 | 653224 | 1306449 | 3266122 |
| 40 | 1 | 199 | 498 | 997 | 1993 | 4984 |
| 40 | 10 | 1993 | 4984 | 9967 | 19935 | 49837 |
| 40 | 100 | 19935 | 49837 | 99674 | 199348 | 498371 |
| 50 | 1 | 82 | 204 | 408 | 817 | 2041 |
| 50 | 10 | 817 | 2041 | 4083 | 8165 | 20413 |
| 50 | 100 | 8165 | 20413 | 40827 | 81653 | 204133 |
| 75 | 1 | 16 | 40 | 81 | 161 | 403 |
| 75 | 10 | 161 | 403 | 806 | 1613 | 4032 |
| 75 | 100 | 1613 | 4032 | 8064 | 16129 | 40322 |
| 100 | 1 | 5 | 13 | 26 | 51 | 128 |
| 100 | 10 | 51 | 128 | 255 | 510 | 1276 |
| 100 | 100 | 510 | 1276 | 2552 | 5103 | 12758 |
| 200 | 1 | | 1 | 2 | 3 | 8 |
| 200 | 10 | 3 | 8 | 16 | 32 | 80 |
| 200 | 100 | 32 | 80 | 159 | 319 | 797 |

Accordingly, in a preferred embodiment described previously, where a 100 cm piece of outlet tubing of 75 microns internal diameter is attached to a 10 cm length of 50 microns inner diameter outlet tube, a pressure differential of 243 mm Hg is generated and measured at the tip of the dialysis probe. In practical situations, due to variabilities in the precise tube diameter, and in the viscosity of the fluid because of impurities, a 10–15 percent variation in the internal pressure was observed.

When constructing a device in accordance with the principles of the present invention, the smallest practical tubing is a 1 cm piece of 25 microns inner diameter tubing. Since the inner diameter of the dialysis fiber membrane used in the preferred embodiment is 215±10 microns, a 200 microns tubing is the largest inner diameter applicable. However, at extremely small fluid flow rates, a smaller diameter tubing can be used. Similarly, if an application requires a flow rate over 250 $\mu$l/min, a larger diameter than 200 microns can be used with an appropriately larger diameter dialysis fiber.

Since the dialysis fiber membrane is supported by fluid pressure, the present invention has three significant advantages over prior dialysis probes:

1. The present invention provides a microdialysis probe which is firm and yet guidable through the tissue rather than damaging the tissue during insertion;

2. It provides more surface area for biological material exchange;

3. Its surface molds to the shape of the surrounding tissue so as to facilitate a more direct interaction.

It is understood of course that the microdialysis probe of the present invention is used with a suitable holder and guide device to aid in insertion of the probe into the living tissue. Such holding and guiding devices are well known and can be readily provided by those skilled in the art.

BRIEF DESCRIPTION OF THE DRAWINGS

The features of this invention which are believed to be novel are set forth with particularity in the appended claims. The invention may be best understood by reference to the following description taken in conjunction with the accompanying drawings, in which like reference numerals identify like elements in the several figures and in which:

FIG. 1 is a perspective view of a preferred loop type embodiment of a microdialysis probe constructed in accordance with the present invention;

FIG. 2 is a cross-sectional view of the microdialysis probe of FIG. 1;

FIG. 3 is a perspective view of another embodiment of the invention;

FIG. 4 is a cross-sectional view of the embodiment of FIG. 3;

FIG. 5 is a perspective view of a further embodiment of the invention; and

FIG. 6 is a cross-sectional view of the embodiment of FIG. 5.

DETAILED DESCRIPTION

Referring now to the drawings, there are illustrated three embodiments of the present invention. FIGS. 1 and 2 illustrate a preferred loop type embodiment. FIGS. 3 and 4 illustrate a side-by-side embodiment. FIGS. 5 and 6 illustrate a concentric embodiment.

It is to be understood that the illustrations and description of embodiments of the present invention are not to be taken as limitations thereof but only as examples of the invention applied to particular structures. It must be understood therefore that the most important aspect of the present invention is the providing of suitable dialysis membrane support means to enable an effective optimum positive pressure to be maintained within the membrane sufficient to reliably self-support and maintain the shape of the membrane during insertion and dialysis sampling without requiring a physical support structure to maintain the membrane shape. Accordingly, all of the embodiments herein illustrated and described utilize fluid pressure for shape retention of the dialysis fiber during insertion as well as sampling in accordance with this important aspect of the present invention.

FIG. 1 illustrates a microdialysis probe 10 which includes an inlet tube 12, an outlet tube 14, and a dialysis fiber membrane 16. Inlet tube 12 delivers a fluid medium under positive fluid pressure from a typical pumping source to the interior of membrane 16. Outlet tube 14 delivers fluid and biological substances from the interior of membrane 16 to a collection vessel or to suitable analytical instruments. Both the inlet and the outlet tube may be constructed of impermeable material such as stainless steel, fused silica, polyimide, etc. It is preferred that the tubes 12 and 14 are formed of extremely thin inner and outer diameter silica tubing coated with polyimide which increases the tubing strength and prevents breaking or kinking of the tube upon bending during use.

Dialysis membrane 16 is a cylindrical section formed of a fiber material which is permeable to compounds of low molecular weight, such as a cellulose acetate dialysis fiber. Fibers of the semipermeable membrane 16 are rigid when they are dry. However, prior to insertion in a biological tissue, the fibers are wetted by the fluid flow through inlet tube 12 and the membrane becomes extremely flaccid. End portion 18 of membrane 16 is adhesively bonded to one end of inlet tube 12. Similarly, the opposite membrane end 20 is adhesively bonded to one end of outlet tube 14. A cynoacrylate adhesive material may be used to attach the membrane to the inlet and outlet tubes.

In order to maintain a continuous fluid flow in the vicinity of the membrane 16, a Teflon coated thin metal wire 22 is placed within the membrane 16 to keep an unrestricted flow of fluid across the tip of the membrane loop. Coated wire 22 is biologically inert and it is preferred that the wire has an external diameter which is smaller than 1/15th of the inner diameter of the cylindrical section forming membrane 16. It is understood that the membrane 16 consisting of a cellulose acetate dialysis fiber enables dialysis of biological substances to take place when the active tip portion 24 of the membrane is inserted into living tissue.

As previously described, a positive fluid pressure of at least about 80 mm Hg inside dialysis membrane 16 is desired as the optimum positive pressure sufficient to reliably support and maintain the shape of membrane 16 during insertion into living tissue and during dialysis sampling without requiring any physical support to maintain the membrane shape. It must be understood that the wire 22 does not provide any skeletal support within membrane 16. The purpose of wire 22 is only to prevent kinking in the membrane loop so as to assure an unrestricted fluid flow across the membrane tip.

When using a cellulose acetate dialysis fiber to form membrane 16, the upper most fluid pressure should be maintained below about 610 mm Hg. Accordingly, such dialysis membranes used in the microdialysis probe 10 of the present invention can maintain enough rigidity in the dialysis fiber to allow insertion and reliable sampling when the positive fluid pressure within the membrane is maintained between about 80–610 mm Hg, and preferably between about 80–500 mm Hg.

As previously described in connection with the Table, the ranges of outlet tubing diameter, fluid flow rates and outlet tubing length which can be utilized to create the desired optimum fluid pressure may be selected from the aforementioned desirable ranges set forth in the Table.

In connection with the preferred loop type embodiment shown in FIGS. 1 and 2, achieving the desired optimum fluid pressure is attained by the diameter of outlet tubing 14 being less than the diameter of inlet tubing 12. Thus, the positive pressure is created by partial restriction of the fluid flow path downstream of the membrane and by adjusting the physical characteristics of the outlet tubing 14 with respect to the desired fluid flow rate.

In the constructed embodiment of this preferred loop type configuration, the inner diameter of tubing 12 was 75 microns whereas the inner diameter of tube 14 was 50 microns of a 10 cm tubing length which was then connected to a 100 cm length of tubing having an inner diameter of 75 microns. In the constructed version, the preferred flow rate was 1–2 µl/min. In accordance with the Table, it would be expected that with these parameters, i.e. an outlet tubing of 50 microns diameter at 10 cm long would provide a positive fluid pressure of about 80–163 mm Hg, to about 161–323 mm Hg when the outlet tubing is also connected to an extended tubing of 100 cm long having an internal diameter of 75 microns. As previously indicated, the measured pressure at the tip of this constructed dialysis probe was found to be 243 mm Hg which falls within the expected range of pressures set forth in the Table for these probe parameters.

In assembling microdialysis probe 10, end 18 of the membrane cylindrical section is mounted over one end of inlet tubing 12. A straight piece of Teflon coated nichrome wire 22 is then inserted through end 20 into the interior of the cylindrical membrane section so as to be completely inside the membrane while holding the assembly together and thereafter mounting membrane end 20 onto one end of outlet tubing 14. Ends 18 and 20 are then respectively adhesively joined to respective tubes 12, 14 and after ensuring that the wire 22 lies symmetrically inside the membrane, the assembly is bent at the middle of the cylindrical membrane section to form a U-shaped loop as shown in FIGS. 1 and 2. A proper length of tubing may then be connected to outlet tubing 14 sufficient to create the desired optimum positive pressure within membrane 16 and the free end of the outlet tubing may be connected to a collection vial or directly to suitable instrumentation. The free end of inlet tubing 12 may of course be connected to a fluid flow regulating pump through any necessary interconnecting length of tubing similar to tubing 12.

Referring now to FIGS. 3 and 4 there is illustrated what may be termed a "side-by-side" microdialysis probe configuration 26 with inlet tube 12 and outlet tube 14 joined together by a connecting sleeve 28 through suitable adhesives. Sleeve 28 may be formed of an impermeable material similar to that used for tubings 12, 14.

In this case, the bottom of probe 26 is formed with a cup-like dialysis fiber membrane 30 having an upper open end 32 adhesively secured to sleeve 28 and a closed bottom end 34. It is understood of course that dialysis membrane 30 may be formed of semipermeable dialysis material similar to that previously described in connection with membrane 16. It is preferred that end 36 of inlet tube 12 extends below end 38 of outlet tube 14 so that inlet tube end 16 penetrates into the interior of membrane 30 somewhat beyond outlet tube end 38 as shown in FIG. 4.

FIGS. 5 and 6 illustrate a concentric microdialysis probe 40 with inlet tube 42 and an outlet tube 44 which from a Y-juncture 46 extends concentrically within the inlet tube. End 32 of cup-like dialysis membrane 30 is adhesively secured to one end of inlet tube 42 and in this case an end 48 of the outlet tube penetrates beyond the end 50 of tube 42 so as to penetrate progressively further into cup-like member 30 and terminate near bottom 34 of the membrane. Y-juncture 46 is suitably adhesively sealed to prevent the undesired loss of fluid.

It is understood of course that the alternative embodiments of FIGS. 3, 4 and 5, 6 are constructed in accordance with the present invention such that there is an effective optimum positive pressure within membrane 30 sufficient to reliably support and maintain the shape of the membrane during insertion and dialysis sampling without requiring a physical support structure to maintain the membrane shape. Thus as previously described, in order to achieve this optimum pressure, a variety of combinations of the parameters involving the outlet tubing diameter and length and/or the flow rate can be used to create the optimum pressure within the dialysis membrane.

In the case of the embodiment of FIGS. 3 and 4, the optimum pressure may be achieved by a partial restriction of the fluid flow beyond membrane 30 by reducing the diameter of outlet tubing 14 as illustrated in FIG. 4. In the embodiment of FIGS. 5 and 6, it can be seen that outlet tubing 44 is necessarily a smaller inner diameter since it is concentrically placed within inlet tubing 42 and therefore the particular diameter size can be chosen in accordance with the principles of the present invention and with the aid of the Table herein to create the desired optimum positive pressure.

The foregoing detailed description has been given for clearness of understanding only, and no unnecessary limitations should be understood therefrom, as modifications will be obvious to those skilled in the art.

What is claimed is:

1. In microdialysis probe apparatus for fluid sampling of biological substances in living tissue, including an inlet tube for continuously delivering a fluid flow under positive fluid pressure to said living tissue, an outlet tube for continuously removing a fluid flow and biological substances from said living tissue, and a semipermeable dialysis fiber membrane at one end of said inlet and outlet tubes for insertion into said living tissue and performing dialysis, the improvement comprising:

membrane support means, including said outlet tube inner diameter bring less than the inner diameter of said inlet tube, and said fluid flow being maintained at a rate with respect to the inner diameter of said outlet tube and the length of said outlet tube sufficient for enabling an effective optimum positive pressure to be maintained within said membrane provided by partial restriction of the continuous fluid flow sufficient to reliably self-support and maintain the shape of said membrane during insertion and dialysis sampling without requiring a physical support to maintain the membrane shape.

2. The improvement of claim 1, wherein said membrane support means enables a positive pressure of at least about 80 mm Hg to be maintained within said membrane.

3. The improvement of claim 2, wherein said membrane support means enables a positive pressure of less than about 610 mm Hg to be maintained within said membrane.

4. The improvement of claim 1, wherein said membrane support means includes said outlet tube having a diameter less than said inlet tube diameter.

5. The improvement of claim 1, wherein said membrane support means comprises a relationship between (a) the length of said outlet tube, (b) the diameter of said outlet tube, and (c) the fluid flow rate sufficient to obtain said effective optimum positive pressure, P, to self-support said membrane said relationship being, $$P = 8\, VLO/\pi R^4$$

where
V is the viscosity of the fluid,
L is the length of the outlet tube,
O is the fluid flow rate; and
R is the inner radius of the outlet tube.

6. The improvement of claim 5, wherein said membrane support means enables a positive pressure of at least about 80 mm Hg to be maintained within said membrane.

7. The improvement of claim 5, including said membrane being a cylindrical shaped member with open ends, and means for forming said membrane into a loop configuration with one loop end communicatively connected to said inlet tube end and the other loop end communicatively connected to said outlet tube end.

8. The improvement of claim 7, including a thin, rigid member within said loop configured membrane to prevent kinking of said membrane during insertion and dialysis sampling.

9. The improvement of claim 5, including said membrane being a cylindrical shaped member with an open end and an opposite closed end, a tubular sleeve surrounding and mounted to said inlet and outlet tubes adjacent said one end thereof, and means for mounting said membrane open end to said tubular sleeve with said inlet tube projecting beyond said one outlet tube end and terminating within said membrane.

10. The improvement of claim 5, including said outlet tube concentrically disposed within said inlet tube, said membrane being a cylindrical shaped member with an open end and an opposite closed end, and means for mounting said membrane open end to said one end of said inlet tube, said outlet tube projecting beyond said inlet tube one end and terminating within said membrane.

11. Microdialysis probe apparatus for fluid sampling of biological substances in living tissue comprising:
an inlet tube for continuously delivering a fluid flow under positive fluid pressure to said living tissue at an inlet tube end;
an outlet tube for continuously removing said fluid flow and biological substances from said living tissue at an outlet tube end;
a U-shaped dialysis fiber membrane having respective legs of the U connected to the inlet tube end and to the outlet tube end; and
membrane support means, including said outlet tube inner diameter being less than the inner diameter of said inlet tube, and said fluid flow being maintained at a rate with respect to the inner diameter of said outlet tube and the length of said outlet tube sufficient for enabling an effective optimum positive pressure to be maintained within said U-shaped membrane provided by partial restriction of the continuous fluid flow sufficient to reliably self-support and maintain the shape of said U-shaped membrane during insertion and dialysis sampling without requiring a physical support to maintain the membrane shape.

12. A microdialysis probe according to claim 11, including a thin, rigid U-shaped wire within said U-shaped membrane to prevent kinking of said U-shaped membrane during insertion and dialysis sampling.

13. A microdialysis probe according to claim 12, wherein said membrane support means enables a positive pressure of at least about 80 mm Hg to be maintained within said U-shaped membrane.

14. A microdialysis probe according to claim 13, wherein said membrane support means enables a positive pressure of less than about 610 mm Hg to be maintained within said U-shaped membrane.

* * * * *

UNITED STATES PATENT AND TRADEMARK OFFICE
CERTIFICATE OF CORRECTION

PATENT NO. : 5,191,900
DATED      : Mar. 9, 1993
INVENTOR(S) : PRAVIN K. MISHRA

It is certified that error appears in the above-indentified patent and that said Letters Patent is hereby corrected as shown below:

On the title page: Item [56] Reference Cited:

Under U.S. PATENT DOCUMENTS, add the following:

```
3,640,269   2/1972   Delgado . . . . . .128/2R
4,221,567   9/1980   Clark, et al. . . .23/230/B
4,694,832   9/1987   Ungerstedt. . . . .128/632
```

Col. 1, line 9,    after "tissue" insert --.--.

Signed and Sealed this

Eighth Day of February, 1994

Attest:

BRUCE LEHMAN

Attesting Officer    Commissioner of Patents and Trademarks